United States Patent
Freeberg (10) Patent No.: US 8,423,142 B2
(45) Date of Patent: *Apr. 16, 2013

(54) CROSS-CHECKING OF TRANSTHORACIC IMPEDANCE AND ACCELERATION SIGNALS

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,560

(22) Filed: Oct. 31, 2011

(65) Prior Publication Data

US 2012/0046559 A1 Feb. 23, 2012

Related U.S. Application Data

(63) Continuation of application No. 10/696,729, filed on Oct. 29, 2003, now Pat. No. 8,050,764.

(51) Int. Cl.
*A61N 1/18* (2006.01)

(52) U.S. Cl.
USPC .............................. 607/42; 607/14; 600/547

(58) Field of Classification Search ................ 607/4–28, 607/42; 600/500–519, 529, 547
See application file for complete search history.

(56) References Cited

U.S. PATENT DOCUMENTS

| | | | |
|---|---|---|---|
| 3,593,718 A | 7/1971 | Krasner | |
| 3,896,817 A | 7/1975 | Hursen et al. | |
| 4,228,803 A | 10/1980 | Rickards | |
| 4,291,699 A | 9/1981 | Geddes et al. | |
| 4,428,378 A | 1/1984 | Anderson et al. | |
| 4,510,944 A | 4/1985 | Porges | |
| 4,519,395 A | 5/1985 | Hrushesky | |
| 4,543,954 A | 10/1985 | Cook et al. | |
| 4,596,251 A * | 6/1986 | Plicchi et al. | 607/20 |
| 4,686,987 A | 8/1987 | Salo et al. | |
| 4,702,253 A | 10/1987 | Nappholz et al. | |
| 4,722,351 A | 2/1988 | Phillipps et al. | |
| 4,773,401 A | 9/1988 | Citak et al. | |

(Continued)

FOREIGN PATENT DOCUMENTS

| | | |
|---|---|---|
| DE | 28 05 482 | 3/1987 |
| EP | 0003567 | 8/1979 |

(Continued)

OTHER PUBLICATIONS

"U.S. Appl. No. 10/696,729, Response filed Jul. 11, 2011 to Final Office Action mailed May 10, 2011", 9 pgs.

(Continued)

*Primary Examiner* — Rex R Holmes
(74) *Attorney, Agent, or Firm* — Schwegman Lundberg & Woessner, P.A.

(57) ABSTRACT

A first chamber minute ventilation rate is determined based on a first transthoracic impedance signal received from a first chamber of a heart and a second chamber minute ventilation rate is determined based on a second transthoracic impedance signal received from a second chamber of the heart. A processor compares the minute ventilation rates to determine a rate. In one embodiment, an accelerometer sensor provides data for evaluating propriety of a rate. Before implementing a rate change, signals from multiple sensors are cross-checked.

20 Claims, 3 Drawing Sheets

U.S. PATENT DOCUMENTS

| | | | |
|---|---|---|---|
| 4,781,201 A | 11/1988 | Wright et al. | |
| 4,827,935 A | 5/1989 | Geddes et al. | |
| 4,830,008 A | 5/1989 | Meer | |
| 4,858,611 A | 8/1989 | Elliott | |
| 4,901,725 A * | 2/1990 | Nappholz et al. | 607/17 |
| 4,930,518 A | 6/1990 | Hrushesky | |
| 4,960,129 A | 10/1990 | dePaola et al. | |
| 4,966,146 A | 10/1990 | Webb et al. | |
| 5,014,698 A | 5/1991 | Cohen | |
| 5,027,813 A | 7/1991 | Pederson et al. | |
| 5,063,927 A | 11/1991 | Webb et al. | |
| 5,074,303 A | 12/1991 | Hauck | |
| 5,085,215 A | 2/1992 | Nappholz et al. | |
| 5,137,019 A | 8/1992 | Pederson et al. | |
| 5,156,147 A | 10/1992 | Warren et al. | |
| 5,179,946 A | 1/1993 | Weiss | |
| 5,190,035 A | 3/1993 | Salo et al. | |
| 5,197,467 A | 3/1993 | Steinhaus et al. | |
| 5,199,428 A | 4/1993 | Obel et al. | |
| 5,201,808 A | 4/1993 | Steinhaus et al. | |
| 5,203,326 A | 4/1993 | Collins | |
| 5,235,976 A | 8/1993 | Spinelli | |
| 5,249,572 A | 10/1993 | Bonnet | |
| 5,269,301 A | 12/1993 | Cohen | |
| 5,271,395 A | 12/1993 | Wahlstrand et al. | |
| 5,273,034 A | 12/1993 | Nilsson | |
| 5,284,136 A | 2/1994 | Hauck et al. | |
| 5,300,093 A | 4/1994 | Koestner et al. | |
| 5,300,094 A | 4/1994 | Kallok et al. | |
| 5,303,702 A | 4/1994 | Bonnet et al. | |
| 5,309,917 A | 5/1994 | Wang et al. | |
| 5,314,449 A | 5/1994 | Lindgren | |
| 5,318,597 A | 6/1994 | Hauck et al. | |
| 5,341,811 A | 8/1994 | Cano | |
| 5,354,317 A | 10/1994 | Alt | |
| 5,379,776 A | 1/1995 | Murphy et al. | |
| 5,391,190 A | 2/1995 | Pederson et al. | |
| 5,423,870 A | 6/1995 | Olive et al. | |
| 5,431,687 A | 7/1995 | Kroll | |
| 5,431,693 A | 7/1995 | Schroeppel | |
| 5,437,285 A | 8/1995 | Verrier et al. | |
| 5,441,524 A | 8/1995 | Rueter et al. | |
| 5,480,412 A | 1/1996 | Mouchawar et al. | |
| 5,507,785 A | 4/1996 | Deno | |
| 5,511,554 A | 4/1996 | Helfenbein et al. | |
| 5,522,860 A | 6/1996 | Molin et al. | |
| 5,524,632 A | 6/1996 | Stein et al. | |
| 5,531,772 A | 7/1996 | Prutchi | |
| 5,540,733 A | 7/1996 | Testerman et al. | |
| 5,560,370 A | 10/1996 | Verrier et al. | |
| 5,562,711 A * | 10/1996 | Yerich et al. | 607/17 |
| 5,562,712 A * | 10/1996 | Steinhaus et al. | 607/20 |
| 5,626,622 A | 5/1997 | Cooper | |
| 5,626,624 A | 5/1997 | Schaldach et al. | |
| 5,685,316 A | 11/1997 | Schookin et al. | |
| 5,700,283 A | 12/1997 | Salo | |
| 5,718,720 A | 2/1998 | Prutchi et al. | |
| 5,722,997 A | 3/1998 | Nedungadi et al. | |
| 5,749,900 A | 5/1998 | Schroeppel et al. | |
| 5,755,671 A | 5/1998 | Albrecht et al. | |
| 5,755,742 A | 5/1998 | Schuelke et al. | |
| 5,792,194 A | 8/1998 | Morra | |
| 5,792,208 A | 8/1998 | Gray | |
| 5,800,467 A | 9/1998 | Park et al. | |
| 5,800,470 A | 9/1998 | Stein et al. | |
| 5,817,135 A | 10/1998 | Cooper et al. | |
| 5,817,136 A | 10/1998 | Nappholz et al. | |
| 5,824,020 A | 10/1998 | Cooper | |
| 5,824,029 A | 10/1998 | Weijand et al. | |
| 5,836,976 A | 11/1998 | Min et al. | |
| 5,836,987 A | 11/1998 | Baumann et al. | |
| 5,842,997 A | 12/1998 | Verrier et al. | |
| 5,891,044 A | 4/1999 | Golosarsky et al. | |
| 5,921,940 A | 7/1999 | Verrier et al. | |
| 5,935,081 A | 8/1999 | Kadhiresan | |
| 5,957,861 A | 9/1999 | Combs et al. | |
| 5,978,707 A | 11/1999 | Krig et al. | |
| 5,978,710 A | 11/1999 | Prutchi et al. | |
| 5,987,356 A | 11/1999 | DeGroot | |
| 6,006,134 A | 12/1999 | Hill et al. | |
| 6,015,388 A | 1/2000 | Sackner et al. | |
| 6,021,351 A | 2/2000 | Kadhiresan et al. | |
| 6,022,322 A | 2/2000 | Prutchi | |
| 6,026,320 A | 2/2000 | Carlson et al. | |
| 6,035,233 A | 3/2000 | Schroeppel et al. | |
| 6,042,548 A | 3/2000 | Giuffre | |
| 6,044,294 A | 3/2000 | Mortazavi et al. | |
| 6,058,331 A | 5/2000 | King | |
| 6,073,048 A | 6/2000 | Kieval et al. | |
| 6,076,015 A | 6/2000 | Hartley et al. | |
| 6,135,970 A | 10/2000 | Kadhiresan et al. | |
| 6,144,878 A | 11/2000 | Schroeppel et al. | |
| 6,151,524 A | 11/2000 | Krig et al. | |
| 6,161,042 A | 12/2000 | Hartley et al. | |
| 6,273,856 B1 | 8/2001 | Sun et al. | |
| 6,278,894 B1 | 8/2001 | Salo et al. | |
| 6,317,632 B1 | 11/2001 | Krig et al. | |
| 6,358,201 B1 | 3/2002 | Childre et al. | |
| 6,370,424 B1 | 4/2002 | Prutchi | |
| 6,371,922 B1 | 4/2002 | Baumann et al. | |
| 6,390,986 B1 | 5/2002 | Curcie et al. | |
| 6,415,183 B1 | 7/2002 | Scheiner et al. | |
| 6,445,951 B1 | 9/2002 | Mouchawar | |
| 6,449,509 B1 | 9/2002 | Park | |
| 6,459,929 B1 | 10/2002 | Hopper et al. | |
| 6,463,326 B1 | 10/2002 | Hartley et al. | |
| 6,473,640 B1 | 10/2002 | Erlebacher | |
| 6,473,644 B1 | 10/2002 | Terry, Jr. et al. | |
| 6,511,438 B2 | 1/2003 | Bernstein et al. | |
| 6,511,500 B1 | 1/2003 | Rahme | |
| 6,512,949 B1 | 1/2003 | Combs et al. | |
| 6,522,914 B1 | 2/2003 | Huvelle | |
| 6,522,924 B1 | 2/2003 | Meier | |
| 6,522,926 B1 | 2/2003 | Kieval et al. | |
| 6,529,772 B2 | 3/2003 | Carlson et al. | |
| 6,561,986 B2 | 5/2003 | Baura et al. | |
| 6,571,121 B2 | 5/2003 | Schroeppel et al. | |
| 6,571,122 B2 | 5/2003 | Schroeppel et al. | |
| 6,611,713 B2 | 8/2003 | Schauerte | |
| 6,647,289 B2 | 11/2003 | Prutchi | |
| 6,690,971 B2 | 2/2004 | Schauerte et al. | |
| 6,795,733 B1 | 9/2004 | Lu | |
| 6,868,346 B2 | 3/2005 | Larson et al. | |
| 6,928,324 B2 * | 8/2005 | Park et al. | 607/20 |
| 6,931,281 B2 | 8/2005 | Bradley et al. | |
| 7,062,326 B2 | 6/2006 | Huvelle et al. | |
| 7,101,339 B2 * | 9/2006 | Daum et al. | 600/529 |
| 7,136,705 B1 * | 11/2006 | Park | 607/27 |
| 7,142,919 B2 * | 11/2006 | Hine et al. | 607/17 |
| 7,395,114 B2 | 7/2008 | Czygan et al. | |
| 8,050,764 B2 * | 11/2011 | Freeberg | 607/42 |
| 2002/0002389 A1 | 1/2002 | Bradley et al. | |
| 2002/0058877 A1 | 5/2002 | Baumann et al. | |
| 2002/0095189 A1 | 7/2002 | Andersson | |
| 2002/0107552 A1 | 8/2002 | Krig et al. | |
| 2002/0107553 A1 | 8/2002 | Hill et al. | |
| 2002/0123768 A1 | 9/2002 | Gilkerson | |
| 2002/0123769 A1 | 9/2002 | Panken et al. | |
| 2002/0147475 A1 | 10/2002 | Scheiner et al. | |
| 2003/0032991 A1 | 2/2003 | Poore | |
| 2003/0069609 A1 | 4/2003 | Thompson | |
| 2003/0105499 A1 | 6/2003 | Hartley et al. | |
| 2003/0114889 A1 | 6/2003 | Huvelle et al. | |
| 2003/0114891 A1 | 6/2003 | Hiebert et al. | |
| 2004/0049237 A1 | 3/2004 | Larson et al. | |
| 2004/0093035 A1 | 5/2004 | Schwartz et al. | |
| 2004/0102908 A1 | 5/2004 | Larson et al. | |
| 2004/0116820 A1 | 6/2004 | Daum et al. | |
| 2005/0004609 A1 | 1/2005 | Stahmann et al. | |
| 2005/0065443 A1 | 3/2005 | Ternes | |
| 2005/0080460 A1 | 4/2005 | Wang et al. | |

FOREIGN PATENT DOCUMENTS

| | | |
|---|---|---|
| EP | 447024 | 9/1991 |
| EP | 0555988 | 8/1993 |
| EP | 702977 A | 3/1996 |
| EP | 0709058 A1 | 5/1996 |

| EP | 765632 | 4/1997 |
| EP | 0940155 | 9/1999 |
| FR | 2305168 | 10/1976 |
| WO | WO-9406512 | 3/1994 |
| WO | WO-9814240 A1 | 4/1998 |
| WO | WO-0044274 A2 | 8/2000 |
| WO | WO-0078391 A1 | 12/2000 |

OTHER PUBLICATIONS

"U.S. Appl. No. 10/696,729 Restriction Requirement mailed Mar. 4, 2009", 6 pgs.
"U.S. Appl. No. 10/696,729, Advisory Action mailed Jun. 12, 2008", 3 pgs.
"U.S. Appl. No. 10/696,729, Final Office Action mailed Jan. 30, 2008", 10 pgs.
"U.S. Appl. No. 10/696,729, Final Office Action mailed May 10, 2011", 7 pgs.
"U.S. Appl. No. 10/696,729, Non final office action mailed Jan. 12, 2007", 10 pgs.
"U.S. Appl. No. 10/696,729, Non final office action mailed Jul. 19, 2007", 10 pgs.
"U.S. Appl. No. 10/696,729, Non Final Office Action mailed Aug. 11, 2009", 9 pgs.
"U.S. Appl. No. 10/696,729, Non Final Office Action mailed Nov. 26, 2010", 7 pgs.
"U.S. Appl. No. 10/696,729, Non-Final Office Action mailed Aug. 7, 2008", 8 pgs.
"U.S. Appl. No. 10/696,729, Non-Final Office Action mailed Jun. 1, 2006", 8 pgs.
"U.S. Appl. No. 10/696,729, Notice of Allowance mailed Aug. 9, 2011", 7 pgs.
"U.S. Appl. No. 10/696,729, Response filed Feb. 28, 2011 to Non Final Office Action mailed Nov. 26, 2010", 14 pgs.
"U.S. Appl. No. 10/696,729, Response filed Apr. 6, 2009 to Restriction Requirement mailed Mar. 4, 2009", 11 pgs.
"U.S. Appl. No. 10/696,729, Response filed Apr. 12, 2007 to Non final office action mailed Jan. 12, 2007", 20 pgs.
"U.S. Appl. No. 10/696,729, Response filed May 29, 2008 to Final Office Action mailed Jan. 30, 2008", 32 pgs.
"U.S. Appl. No. 10/696,729, Response filed Oct. 31, 2006 to Non-Final Office Action mailed Jun. 1, 2006", 16 pgs.
"U.S. Appl. No. 10/696,729, Response filed Oct. 18, 2007 to Non-Final Office Action mailed Jul. 19, 2007", 33 pgs.
"U.S. Appl. No. 10/696,729, Response filed Nov. 7, 2008 to Non-Final Office Action mailed Aug. 7, 2008", 26 pgs.
"U.S. Appl. No. 10/696,729, Response filed Nov. 12, 2009 to Non Final Office Action mailed Aug. 11, 2009", 12 pgs.
"Heart rate variability. Standards of measurement, physiological interpretation, and clinical use. Task Force of the European Society of Cardiology and the North American Society of Pacing and Electrophysiology.", European Heart Journal, 17, Prepared by the Task Force of the European Society of Cardiology and the North American Society of Pacing and Electrophysiology; published by the American Heart Association, Inc.; European Society of Cardiology, (1996), 354-381.
"Heart rate variability: standards of measurement, physiological interpretation and clinical use. Task Force of the European Society of Cardiology and the North American Society of Pacing and Electrophysiology", Circulation, 93(5), (Mar. 1, 1996), 1043-1065.
Behrens, S., "Effects of Amiodarone on the Circadian Pattern of Sudden Cardiac Death (Department of Vererans Affairs Congestive Heart Failure-Survival Trial of Antiarrhythmic Therapy)", Am. J. Cardiol., 80(1), (Jul. 1997), 45-48.
Behrens, S., "Modification of the Circadian Pattern of Ventricular Tachyarrhythmias by Beta-Blocker Therapy", Clin. Cardiol., 20(3), (Mar. 1997), 253-257.
Berger, R. D., "An Efficient Algorithm for Spectral Analysis of Heart Rate Variability", IEEE Transactions on Biomedical Engineering, BME-33 (9), (Sep. 1986), 900-904.
Bigger, J. T., "Correlations Among Time and Frequency Domain Measures of Heart Period Variability Two Weeks After Acute Myocardial Infarction", Arrhythmias and Conduction Disturbances, 69, (Apr. 1, 1992), 891-898.

Bigger, Jr., J. T., "Spectral Analysis of R-R Variability to Evaluate Autonomic Physiology and Pharmacology and to Predict Cardiovascular Outcomes in Humans", Diagnostic Evaluation, Part XI, Chapter 101, (1992), 1151-1170.
Bilgutay, A M, et al., "A new concept in the treatment of hypertension utilizing an implantable electronic device: "Baropacer"", Trans Am Soc Artif Intern Organs., 10, (1964), 387-395.
Bilgutay, A M, et al., "Vagal tuning for the control of supraventricular arrhythmias", Surgical Forum, 16, (1965), 151-3.
Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.
Bocker, D., "Ventricular Resynchronization Therapy May Restore Autonomic Balance as Evidenced by Reducing the Low Frequency to High Frequency Autonomic Ratio in Heart Failure Patients", 4th International Meeting organized by the Working Group on Heart Failure of the European Society of Cardiology (Abstract), Barcelona, Spain, (Jun. 11, 2001), 1 p.
Borst, C, et al., "Optimal frequency of carotid sinus nerve stimulation in treatment of angina pectoris", Cardiovascular Research, 8(5), (Sep. 1974), 674-80.
Braunwald, E, et al., "Carotid sinus nerve stimulation in the treatment of angina pectoris and supraventricular tachycardia", California Medicine, 112(3), (Mar. 1970), 41-50.
Braunwald, E, et al., "Relief of angina pectoris by electrical stimulation of the carotid-sinus nerves", New England Journal of Medicine, 277(24), (Dec. 14, 1967), 1278-83.
Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.
Courtice, G P, et al., "Effect of frequency and impulse pattern on the non-cholinergic cardiac response to vagal stimulation in the toad, Bufo marinus", Journal of the Autonomic Nervous System, 48(3), (Aug. 1994), 267-72.
Crawford, Michael H., et al., "ACC/AHA Guidelines for Ambulatory Electrocardiography. A report of the American College of Cardiology/American Heart Association Task Force on Practice Guidelines (Committee to Revise the Guidelines for Ambulatory Electrocardiography). Developed in collabo", J Am Coll Cardiol., 34(3), (Sep. 1999), 912-48.
Dart, Jr., C H, et al., "Carotid sinus nerve stimulation treatment of angina refractory to other surgical procedures", Annals of Thoracic Surgery, 11(4), (Apr. 1971), 348-59.
De Landsheere, D, et al., "Effect of spinal cord stimulation on regional myocardial perfusion assessed by positron emission tomography", American Journal of Cardiology, 69(14), (May 1, 1992), 1143-9.
Epstein, S. E., et al., "Treatment of angina pectoris by electrical stimulation of the carotid-sinus nerves", New England Journal of Medicine, 280(18), (May 1, 1969), 971-978.
Farrehi, C, "Stimulation of the carotid sinus nerve in treatment of angina pectoris", American Heart Journal, 80(6), (Dec. 1970), 759-65.
Feliciano, L, et al., "Vagal nerve stimulation releases vasoactive intestinal peptide which significantly increases coronary artery blood flow", Cardiovascular Research, 40(1), (Oct. 1998), 45-55.
Freeberg, S., "Automatically Configurable Minute Ventilation Sensor", U.S. Appl. No. 10/735,598, filed Dec. 12, 2003, 35 pgs.
Fromer, M, et al., "Ultrarapid subthreshold stimulation for termination of atrioventricular node reentrant tachycardia", Journal of the American College of Cardiology, 20(4), (Oct. 1992), 879-83.
Hauck, John A., "A Minute Ventilation Sensor Derived from Intrathoracic Electric Impedance as a Cardiac Pacemaker Rate Modulator", University of Minnesota Master Thesis, (Jun. 1993), pp. 80-86 & 97.
Hayano, J., et al., "Circadian rhythms of atrioventricular conduction properties in chronic atrial fibrillation with and without heart failure.", J Am Coll Cardiol., 31(1), (Jan. 1998), 158-166.
Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.

Henning, R J, et al., "Vagal nerve stimulation increases right ventricular contraction and relaxation and heart rate", Cardiovascular Research, 32(5), (Nov. 1996), 846-53.

Henning, R J, et al., "Vagal stimulation attenuates sympathetic enhancement of left ventricular function", American Journal of Physiology, 258(5 Pt 2), (May 1990), H1470-5.

Jackson, Leland B., "Chapter 11 / Quantization Effects", Digital Filters and Signal Processing, 2d Edition, Kluwer Academic Publishers, (1989), pp. 297-340.

Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1999;83(4):642, (Oct. 15, 1998), 921-6.

Kim, J., et al., "Cardiac Cycle Synchronized Sampling of Impedance Signal", U.S. Appl. No. 10/612,388, filed Jul. 2, 2003, 28 pgs.

Krig, David B., "Apparatus and Method for Treating Ventricular Tachyarrhythmias", U.S. Appl. No. 11/073,818, filed Mar. 7, 2005, 61 pgs.

Lavery, C. E., "Nonuniform Nighttime Distribution of Acute Cardiac Events", Circulation, 96(10), (Nov. 18, 1997), 3321-3327.

Mannheimer, C, et al., "Epidural spinal electrical stimulation in severe angina pectoris", British Heart Journal, 59(1), (Jan. 1988), 56-61.

Mannheimer, C, et al., "Transcutaneous electrical nerve stimulation (TENS) in angina pectoris", Pain, 26(3), (Sep. 1986), 291-300.

Mannheimer, C, et al., "Transcutaneous electrical nerve stimulation in severe angina pectoris", European Heart Journal, 3(4), (Aug. 1982), 297-302.

Mazgalev, T N, et al., "Autonomic modification of the atrioventricular node during atrial fibrillation: role in the slowing of ventricular rate", Circulation, 99(21), (Jun. 1, 1999), 2806-14.

Murphy, D F, et al., "Intractable angina pectoris: management with dorsal column stimulation", Medical Journal of Australia, 146(5), (Mar. 2, 1987), 260.

Peckova, M., "Circadian Variations in the Occurrence of Cardiac Arrests", Circulation, 98 (1), (1998), pp. 31-39.

Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.

Peters, T K, et al., "The principle of electrical carotid sinus nerve stimulation: a nerve pacemaker system for angina pectoris and hypertension therapy", Annals of Biomedical Engineering, 8(4-6), (1980), 445-58.

Schauerte, P, et al., "Catheter stimulation of cardiac parasympathetic nerves in humans: a novel approach to the cardiac autonomic nervous system", Circulation, 104(20), (Nov. 13, 2001), 2430-5.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Transvenous Parasympathetic Nerve Stimulation in the Inferior Vena Cava and Atrioventricular Conduction", Journal of Cardiovascular Electrophysiology, 11(1), (Jan. 2000), 64-69.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Takahashi, N, et al., "Vagal modulation of ventricular tachyarrhythmias induced by left ansae subclaviae stimulation in rabbits", Japanese Heart Journal, 39(4), (Jul. 1998), 503-11.

Vanoli, E., et al., "Vagal Stimulation and Prevention of Sudden Death in Conscious Dogs With a Healed Myocardial Infarction", Circulation Research, 68(5), (May 1991), 1471-1481.

Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.

Waninger, M S, et al., "Electrophysiological control of ventricular rate during atrial fibrillation", Pacing & Clinical Electrophysiology, 23(8), (Aug. 2000), 1239-44.

Yamashita, T., "Circadian Variation of Paroxysmal Atrial Fibrillation", Circulation, 96(5), (Sep. 2, 1997), 1537-1541.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

* cited by examiner

CROSS-CHECKING OF TRANSTHORACIC IMPEDANCE AND ACCELERATION SIGNALS

CLAIM OF PRIORITY

This application is a continuation of and claims the benefit of priority under 35 U.S.C. §120 to U.S. patent application Ser. No. 10/696,729, entitled "CROSS-CHECKING OF TRANSTHORACIC IMPEDENCE AND ACCELERATION SIGNALS," filed on Oct. 29, 2003, now U.S. Pat. No. 8,050,764 which is hereby incorporated by reference herein in its entirety.

RELATED APPLICATIONS

This document is related to and commonly assigned U.S. Provisional Patent Application Ser. No. 60/437,356, entitled "AUTOMATICALLY CONFIGURABLE MINUTE VENTILATION SENSOR," inventor Scott Freeberg, filed Dec. 30, 2002, the specification of which is hereby incorporated by reference in its entirety.

This document is related to and commonly assigned U.S. patent application Ser. No. 10/268,023, entitled "RATE ADAPTIVE CARDIAC RHYTHM MANAGEMENT DEVICE USING TRANSTHORACIC IMPEDANCE," filed Oct. 8, 2002, abandoned, which is a continuation of U.S. patent application Ser. No. 09/492,912, filed Jan. 20, 2000, now U.S. Pat. No. 6,463,326, which is a continuation of U.S. patent application Ser. No. 09/316,690, filed May 21, 1999, now U.S. Pat. No. 6,161,042, which is a divisional of U.S. patent application Ser. No. 09/032,731, filed Feb 27, 1998, now U.S. Pat. No. 6,076,015, the specifications of which are each incorporated by reference herein.

TECHNICAL FIELD

This document relates generally to transthoracic minute ventilation and acceleration for purposes of cardiac rhythm management and in particular, but not by way of limitation, to detection and discrimination of arrhythmias in an implantable medical device.

BACKGROUND

Implantable medical devices are used for treating cardiac dysfunction. Cardiac pacemakers, for example, are implantable medical devices that replace or supplement a heart's compromised ability to pace itself by delivering electrical pacing pulses to the heart.

Rate controlled pacemakers are operated in accordance with a measured physiological variable that corresponds to exertion level and is reflective of the body's metabolic rate. Minute ventilation is an indicator of the rate of oxygen consumption and thus, exertion level. Minute ventilation corresponds to the amount of air breathed by a subject over a minute, or other specified period of time, and can be computed as the product of respiratory rate and tidal volume.

An impedance measurement technique is sometimes used for measuring minute ventilation. The blood and body fluids within the thoracic cavity constitute a volume conductor. The electrical impedance between two points in the thoracic cavity is dependent upon the volume of blood or air between those points. The impedance can be measured by generating a constant current field within the cavity and then measuring the potential difference between the two points.

Interference with the impedance signal, for example, by environmental noise, however, can compromise the ability of the impedance measurement to accurately reflect the patient's actual ventilation. Interference may also result from an intermittent lead, poor lead placement, lead maturation, lead migration or a poor baseline. Such interference may result in delivery of improper pacing. For example, a dislodged lead may erroneously call for an increased pacing rate. As another example, an increased pacing rate may be indicated by an accelerometer responding to a bump detected while driving in an automobile.

SUMMARY

The present subject matter provides an implantable cardiac rhythm management device adapted to measure minute ventilation and a physical activity level. For example, in one embodiment, a first minute ventilation rate is determined based on a transthoracic impedance measured in a first chamber (for instance, an atrial chamber) of the heart and second minute ventilation rate is determined based on a transthoracic impedance measured in a second chamber (for instance a ventricular chamber) of the heart. As a consequence of the two ventilation rates, the actual rate response of therapy is adjusted. In one embodiment, the second minute ventilation rate is used to confirm the appropriateness of therapy before the altering the sensor driven rate.

The present subject matter includes structures and methods for receiving multiple input signals (for example, multiple chamber minute ventilation rates and accelerometers) and selecting appropriate inputs based on comparing the different input signals. Aberrant input signal sources are selectively disabled, discarded or disregarded.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present subject matter. The following detailed description is, therefore, not to be taken in a limiting sense, and the scope of the present invention is defined by the appended claims and their equivalents.

This document discloses, among other things, systems, method and apparatus involving cardiac rhythm management systems used for sensing a cardiac signal, including intracardiac electrogram or surface electrocardiogram (ECG). Such cardiac rhythm management systems include, but are not limited to, pacemakers, cardiac resynchronization therapy (CRT) devices, cardioverter/defibrillators, pacer/defibrillators, and drug delivery devices. However, it is to be understood that the present methods and apparatuses of compressing a signal can be applied to heart beat detection as well as other signals related to cardiac activities, including, but not being limited to, mechanical motion, sound, pressure, acceleration, and impedance signals.

Normally, the sensor driven rate from atrial minute ventilation is nearly identical to that of the sensor driven rate from ventricular minute ventilation, however electrode problems and cardiac health can produce measurable differences in the ventilation rates.

In one embodiment, a primary minute ventilation sensor is used to determine therapy and after a predetermined number of measurement cycles, a secondary minute ventilation sensor is measured. The primary minute ventilation sensor is configured to measure transthoracic impedance in first chamber of a heart and the secondary minute ventilation sensor is configured to measure transthoracic impedance in a second chamber of the heart. If the rate from the primary sensor differs from the rate of the secondary sensor, then this is an indication of an anomaly. In one embodiment, a third sensor is used to cross check performance of the first sensor and second sensor and determine which sensor is to be ignored or discounted. In one embodiment, an error code is generated and stored. In one embodiment, an alert signal is generated and communicated to an external device or programmer. In one embodiment, on detecting a difference, the most recent pacing rate is maintained despite the disagreement in sensor readings. For example, in the event that the sensor rates differ, the primary minute ventilation sensor rate calculation is frozen for that particular cycle. By maintaining the current pacing rate, the patient can avoid a rate bump caused by the alternate chamber measurement.

In one embodiment, minute ventilation sensor data is stored from both the primary and secondary chamber. The stored data is available for further analysis and cross checking.

The transthoracic impedance is measured using a first set of electrodes responsive to a first chamber of a heart and using a second set of electrodes responsive to a second chamber of the heart. The impedance signals received from each set of electrodes are processed to determine a minute ventilation rate. The physical activity level is measured by an accelerometer disposed in the implanted device.

Minute ventilation data and acceleration data is crosschecked to determine appropriateness of a pacing rate delivered to the heart. A sensor providing a signal inconsistent with signals received from other sensors is disregarded in determining a pacing rate. In various embodiments, pacing may be interrupted, decelerated or accelerated depending on the sensor signals.

Figure 1:
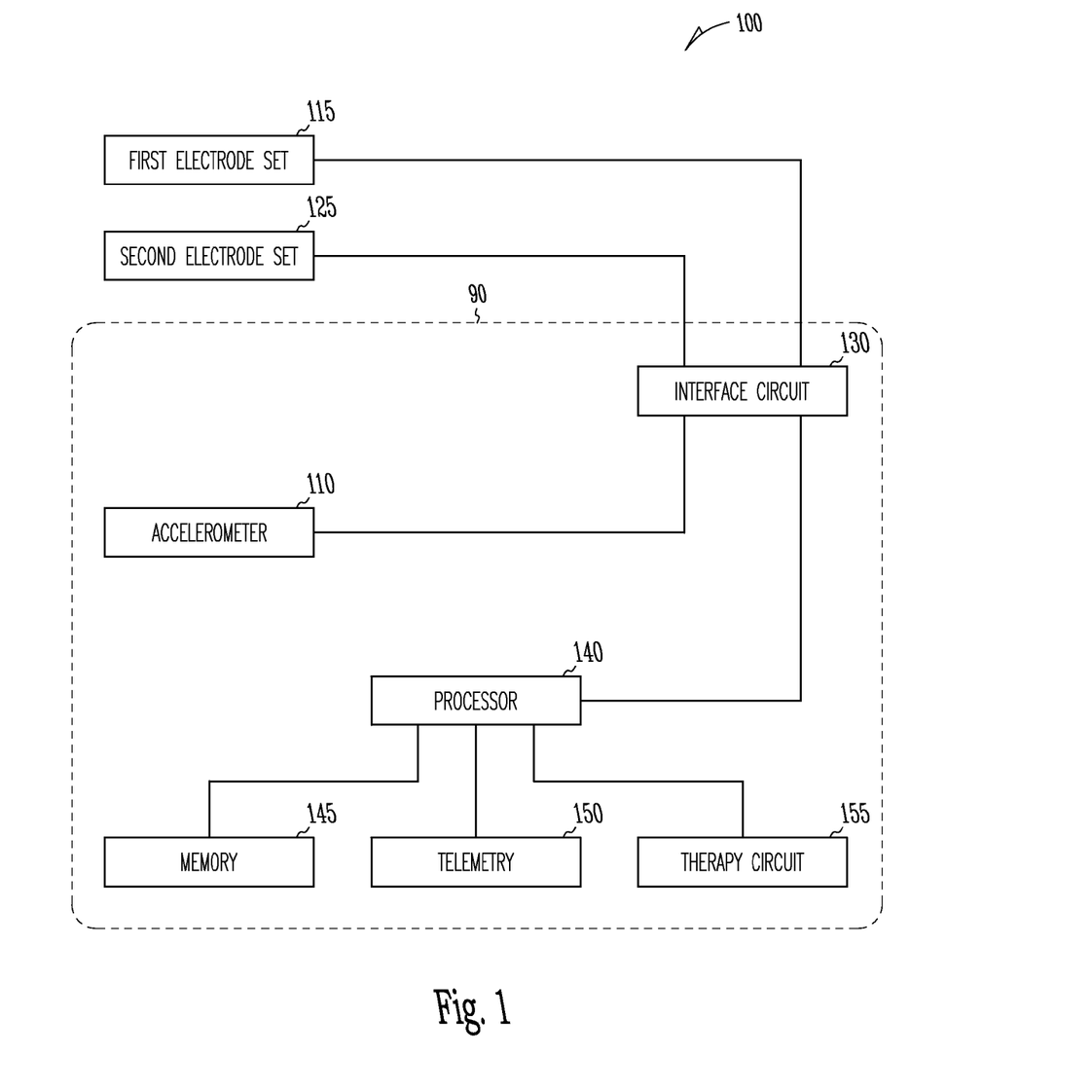
FIG. 1 illustrates a block diagram of an implantable cardiac rhythm management system according to one embodiment of the present subject matter.

FIG. 1 illustrates a block diagram of system 100 according to one embodiment of the present subject matter. In the figure, interface circuit 130 is coupled to first electrode set 115, second electrode set 125, accelerometer 110 and processor 140. Processor 140 is also coupled to memory 145, telemetry module 150 and therapy circuit 155.

Selected components of system 100 are housed within a hermetically sealed container of housing 90. In one embodiment, system 100 is suitable for implantation in a body. For example, in one embodiment, housing 90 is coupled to first electrode set 115 and second electrode set 125 by at least one lead.

First electrode set 115 is configured to receive a transthoracic signal associated with a first chamber of a heart. The chambers of the heart include the right atrium, the right ventricular, the left atrium and the left ventricular. In one embodiment, first electrode set 115 is configured to determine an impedance in an atrial chamber. Impedance is determined by sensing a voltage between a first pair of electrodes while a field is generated by a current applied using a second pair of electrodes.

In one embodiment, first electrode set 115 includes electrodes for generating a transthoracic excitation current field and electrodes for sensing a voltage. For example, in one embodiment, the current source is generated between a lead ring electrode and a first conductive surface of housing 90 (sometimes referred to as a case electrode) and a voltage is sensed between a second conductive surface of housing 90 (sometimes referred to as an indifferent electrode) and lead tip.

First electrode set 115 is positioned to both generate the excitation field and sense a voltage within a first chamber of the heart. A voltage detected by first electrode set 115 is supplied to interface circuit 130.

Second electrode set 125 is configured to receive a transthoracic signal associated with a second chamber of the heart. As with first electrode set 115, second electrode set 125 includes a number of electrodes, including, for example, a tip electrode, a ring electrode, a case electrode and an indifferent electrode. In one embodiment, first electrode set 115 and second electrode set 125 share one or more electrodes in common and they differ in the placement of the individual tip and ring electrodes used for generating a excitation current field and sensing voltages. As with first electrode set 115, second electrode set 125 is coupled to interface circuit 130.

In one embodiment, first electrode set 115 and second electrode set 125 are both coupled to the same chamber of the heart.

Interface circuit 130 provides a coupling between first electrode set 115 and second electrode set 125 and processor 140. In various embodiments, interface circuit 130 includes any combination of a MOS switching matrix, an analog to digital converter, a digital to analog converter, an amplifier, channel interfaces, a signal processor, a comparator, a demodulator, a counter, a clock, a processor or other circuitry. In one embodiment, interface circuit 130 includes an exciter circuit configured to provide a transthoracic excitation current field. The exciter circuit is controlled by processor 140.

Accelerometer 110, in one embodiment, includes an integrated silicon element that is bonded to a ceramic circuit board within housing 90 having a mass flexibly supported by four leaf springs attached to a frame. The leaf springs each include a piezoresistive element which forms the four legs of a Wheatstone bridge. The bridge becomes unbalanced when the mass is displaced by an acceleration force in a direction perpendicular to the frame.

The Wheatstone bridge is energized in a pulse mode by a predetermined voltage applied for a short period of time and at a predetermined repetition rate. The output from accelerometer 110 is amplified and filtered to remove motion artifacts from noise sources while allowing passage of signal components whose frequencies are related to body motion due to physical activity. The output from the band-pass filter is digitized and signal processed. In one embodiment, interface circuit 130 includes an amplifier, a filter and an analog-to-digital converter and signal processing is performed by processor 140.

In one embodiment, interface circuit 130 both supplies an excitation current and receives a voltage signal via electrodes of first electrode set 115 and second electrode set 125. In addition, interface circuit 130 receives an acceleration signal from accelerometer 110. As a function of the signals received by the first electrode set 115, second electrode set 125 and accelerometer 110, a digital output signal is supplied to processor 140.

Interface circuit 130 and processor 140 operate together to detect changes in transthoracic impedance within the heart. Impedance is measured by sending a low level oscillating electrical signal to selected electrodes of first electrode set 115 or second electrode set 125. The oscillating electrical signal is modulated by the activity of the heart chamber to which the electrode set is connected. The modulated signal is then detected, amplified and demodulated to remove the modulation signal. The remaining envelope signal corresponds to an analog measure of instantaneous impedance as a function of time.

The instantaneous impedance signal is digitized. In one embodiment, the digitized impedance versus time signal is subjected to further filtering or signal processing.

Memory 145 provides program and data storage for processor 140. The program stored in memory 145, and executed by processor 140, is configured to cause system 100 to perform a method as described elsewhere in this document. Stored data may include parameters for providing an excitation signal, measured voltages and signals, impedance measurements, timing information, acceleration information and other data.

Telemetry 150 allows system 100 to wirelessly communicate with an external programmer. Telemetry 150 may include an inductive loop coupling coil, a radio frequency antenna or other means of transdermally communicating. In one embodiment, telemetry 150 allows uni-directional communication and thus, data from system 100 can be transmitted to an external programmer or other device. In one embodiment, telemetry 150 allows bi-directional communication and thus, data or programming can be transmitted to system 100 in addition to allowing data to be transmitted from system 100.

Therapy circuit 155 provides therapy to the heart or other organ as a function of a signal received from processor 140. In one embodiment, therapy circuit 155 includes a pulse generator and provides an electrical signal to the heart. The electrical signal, in one embodiment, is provided to the heart via either first electrode set 115, second electrode set 125, or by another electrode set. In one embodiment, therapy circuit 155 includes a drug delivery circuit configured to release a medicament into an organ of the body.

Figure 2:
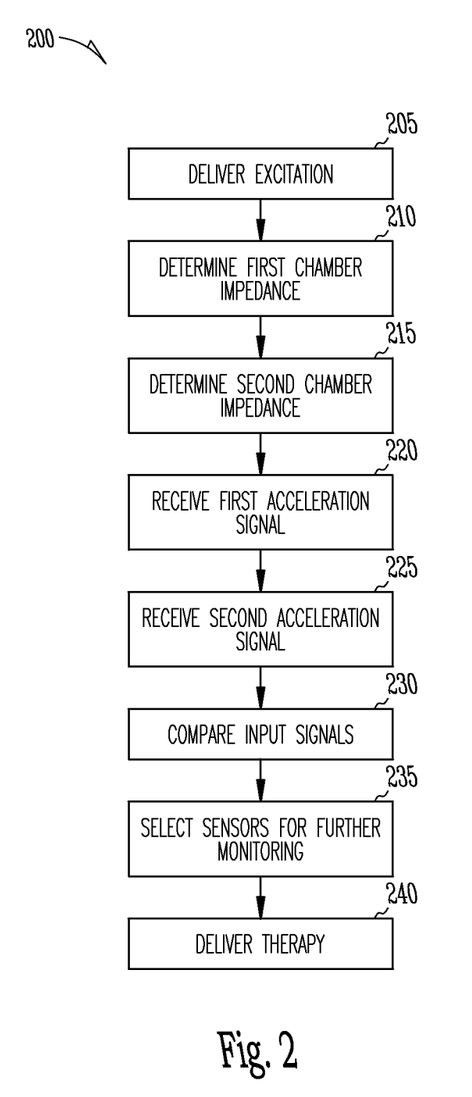
FIG. 2 illustrates a method according to one embodiment of the present subject matter.

FIG. 2 illustrates method 200 according to one embodiment of the present subject matter. At 205, an excitation field is generated in the heart. A current is delivered using two conductors of the electrode set. The excitation field may be generated in one, two or more chambers of the heart. The field is cycled to and if applied to multiple chambers of the heart, the field is modulated at different frequencies that can be subsequently demodulated and filtered.

At 210, the transthoracic impedance of the first chamber is measured using two conductors of the electrode set. The impedance is measured by sensing a voltage generated as a consequence of the heart activity and the excitation field. At 215, the transthoracic impedance of the second chamber is measured.

At 220, a first acceleration signal is generated, and at 225, a second acceleration signal is generated. The acceleration signals are derived from semiconductor structures disposed within the implanted device. In one embodiment, the acceleration signals are derived from accelerometers having aligned axis of sensitivity. In one embodiment, the acceleration signals are derived from accelerometers having axis of sensitivity that are perpendicular, or otherwise not aligned.

At 230, the input signals are compared. The input signals include the first chamber minute ventilation rate, the second chamber minute ventilation rate, the first accelerometer signal and the second accelerometer signal. In one embodiment, a program executing on processor 140 performs the comparison and determines a rate for further pacing. In various embodiments, different algorithms are executed in selecting a pacing rate as a function of the input signals.

At 235, in one embodiment, processor 140 selects sensors for further monitoring and deselects those sensors generating incorrect data. Therapy is delivered at 240 as a function of the data generated by the selected sensors.

Multiple input signals affords the opportunity to implement different algorithms for establishing a pacing rate. In one embodiment, the algorithm to be implemented is remotely programmable and remotely selectable by wireless communication conducted via telemetry 150. For example, in one embodiment, the pacing rate is determined independent of the first chamber minute ventilation rate and the second chamber minute ventilation rate at times when the ventilation rates are not in agreement. In one embodiment, an algorithm is executed to determine which chamber is providing an appropriate ventilation rate and pacing is delivered as a function of the rate from the selected chamber. In one embodiment, a pacing rate is adjusted based on the differences between the measured ventilation rates in the different chambers. In one embodiment, adjustments to therapy are precluded based on differences between the measured ventilation rates in the different chambers.

In one embodiment, the first chamber minute ventilation rate and the second chamber minute ventilation rate is cross checked with a first acceleration signal from a first accelerometer. In one embodiment, the first chamber minute ventilation rate and the second chamber minute ventilation rate is cross checked with both a first acceleration signal from a first accelerometer and a second acceleration signal from a second accelerometer.

In one embodiment, a first accelerometer signal and a second accelerometer signal is cross checked with a first chamber minute ventilation rate. In one embodiment, the first accelerometer signal and the second accelerometer signal is cross checked with both a first chamber minute ventilation rate and a second chamber minute ventilation rate.

In one embodiment, if the response from the active chamber minute ventilation sensor is similar to the response from the inactive chamber minute ventilation sensor, for a particular minute ventilation tidal volume (or respiratory rate), then processor executes an algorithm to determine that the rate from the active sensor is appropriate.

In one embodiment, if the minute ventilation rate from the first chamber is substantially different than that of the second chamber rate, then the processor executes a program to determine which rate is appropriate. In one embodiment, an accelerometer signal is used to cross-check a minute ventilation rate. For example, if the minute ventilation rates from both chambers is not in agreement, then the accelerometer signal is used as an arbiter to determine which minute ventilation rate is appropriate. For instance, at a time when a first minute ventilation signal indicates a high rate and a second minute ventilation signal indicates a generally normal level, then the data from the accelerometer is used to determine which of the two minute ventilation signals is more reliable.

In one embodiment, if the data indicates that the patient is experiencing respiratory distress (as indicated by a high respiratory rate, gasping or a high tidal volume), then, the present subject matter is programmed to suspend attempts to elevate the minute ventilation driving pacing rate.

In one embodiment, if the active chamber minute ventilation response is resulting in a high rate pacing, (for example, at maximum sensor rate) and if the inactive chamber minute ventilation response would have resulted in moderate pacing, then the present subject matter is programmed to determine whether to use the active chamber minute ventilation rate. In addition, an acceleration signal may be used to cross-check the selected rate.

In one embodiment, if an active minute ventilation sensor is driven at a high rate, (such as maximum sensor rate) and an inactive sensor response yielding a moderate rate and an accelerometer indicates a moderate response, then the present subject matter would indicate that a high pacing rate is inappropriate.

Figure 3:
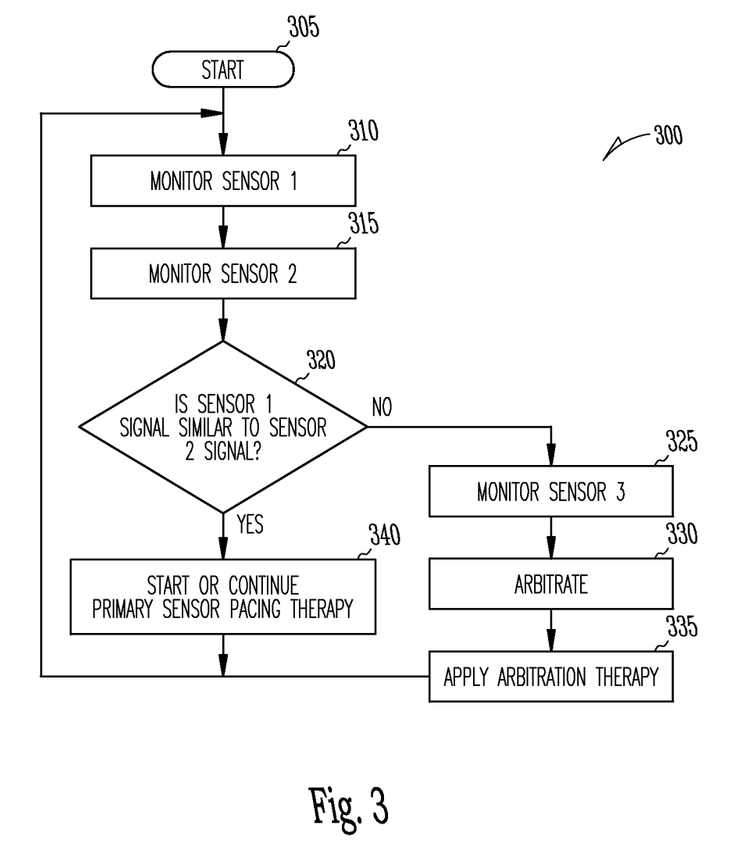
FIG. 3 illustrates a method according to one embodiment of the present subject matter.

FIG. 3 illustrates method 300 according to one embodiment of the present subject matter. Method 300 begins at 305 and proceeds with monitoring of a first sensor at 310 and a second sensor at 315. At 320, a query is evaluated to determine if the first sensor signal is similar to the second sensor signal. If sufficiently similar, then, at 340, a pacing therapy (as determined by a primary sensor) is either started or continued. In one embodiment, the primary sensor is either the first or second sensor. If the signals from the first and second sensors are not sufficiently similar, then a signal from a third sensor is monitored as shown at 325. At 330, the signal from the third sensor is used to arbitrate between the first and second sensor. In one embodiment, data from other sensors is used to arbitrate amongst the signals from the first, second and third sensors. As a consequence of the arbitration determination, an arbitration therapy regimen is selected and delivered as shown at 335. Following delivery of the arbitration therapy (at 335) or delivery of the primary sensor pacing therapy (as shown at 340), processing continues and returns to monitoring the first and second sensor, at 310 and 315 respectively.

Other configurations are also contemplated. For example, in one embodiment, therapy is delivered according to a signal received from a first sensor and after a predetermined time, a signal from a second sensor is used to cross-check the first sensor. If the signal from the second sensor is substantially different, then a third sensor, of a different type, is used to cross-check and determine if the first or second sensor signal is the more reliable signal. Therapy is delivered based on the determination of which sensor is more reliable. In one embodiment, data from other sources may also be used in evaluating the propriety of any particular sensor.

In various embodiments, the first, second and third sensors are any combination of sensors including impedance sensors (minute ventilation) and accelerometers.

Alternative Embodiments

In one embodiment, the excitation signal is applied to alternate chambers of the heart. In one embodiment, the present subject matter monitors a particular minute ventilation rate derived from a selected chamber until such time that the sensor provides inappropriate information, as determined by a comparison with a second chamber or from a second sensor. In one embodiment, the present subject matter monitors two or more sensors (or chambers), either alternately or substantially simultaneously. Simultaneous monitoring of minute ventilation, in one embodiment, entails using different excitation frequencies and discerning the different chambers by filtering.

In addition to accelerometer sensors, other sensors are also contemplated for cross-checking the data from the minute ventilation rate sensors. For example, in one embodiment, a blood pressure sensor provides a signal for cross-checking. Such sensors may be described as an adaptive rate therapy sensor, other examples of which include a respiratory sensor, a QT interval sensor, a contractility sensor and a depolarization sensor.

According to the present subject matter, for example, a minute ventilation signal (either derived from one or two chambers) is used to cross-check an accelerometer sensor signal. According to one embodiment, for example, an accelerometer sensor signal (derived from one or two accelerometers) is used to cross-check a minute ventilation signal (derived from either one or two chambers).

In one embodiment, a first and second accelerometer are included within housing 90. A second accelerometer serves as a back-up for a first accelerometer.

In one embodiment, a first and second accelerometer are included within housing 90. The first accelerometer has an axis of sensitivity aligned along a first direction and the second accelerometer has an axis of sensitivity aligned along a second direction. The first direction differs from the second direction.

In various embodiments, processor 140 includes a digital signal processor, a microprocessor, an analog processor, logic gates, and analog circuitry.

An accelerometer provides an acceleration signal in response to a detected acceleration. In one embodiment, the accelerometer is disposed within an implanted medical device and provides an acceleration signal associated with an acceleration of the medical device. Thus, an acceleration experienced by the body of the patient, in general, or a particular organ, specifically, will yield an acceleration signal.

A minute ventilation sensor, as described herein, provides a measure of a breathing rate based on a transthoracic impedance measurement associated with a particular chamber of the heart. For example, in one embodiment, the housing of an implanted medical device serves as one electrode for measuring the impedance and a second electrode is coupled to circuitry within the medical device. The particular chamber of the heart for which a transthoracic impedance is associated is determined by placement of the second electrode.

CONCLUSION

The above description is intended to be illustrative, and not restrictive. Many other embodiments will be apparent to those of skill in the art upon reviewing the above description.

What is claimed is:

1. An implantable system configured to be coupled to a heart having a first chamber and a second chamber, the system comprising:
 a first impedance sensor configured to measure a first impedance associated with the first chamber;
 a second impedance sensor configured to measure a second impedance associated with the second chamber; and
 a processor coupled to the first impedance sensor and the second impedance sensor, the processor configured to determine a first ventilation rate using the first impedance, determine a second ventilation rate using the second impedance, and compare the first ventilation rate to the second ventilation rate to determine a difference between the first ventilation rate and the second ventilation rate.

2. The system of claim 1, further comprising an activity sensor coupled to the processor, the activity sensor configured to sense an activity signal indicative of physical activity, and wherein the processor is configured to select one of the first impedance and the second impedance using the activity signal and the difference between the first ventilation rate and the second ventilation rate.

3. The system of claim 2, wherein the activity sensor comprises an accelerometer.

4. The system of claim 3, further comprising a therapy circuit coupled to the processor, the therapy circuit configured to deliver a therapy to the heart, and wherein the processor is configured to control the delivery of the therapy using the selected one of the first impedance and the second impedance.

5. The system of claim 4, wherein the therapy circuit comprises a pulse generator.

6. The system of claim 1, further comprising a therapy circuit coupled to the processor, and wherein the processor is configured to provide a first therapy signal to the therapy circuit in response to the first ventilation rate not being substantially different from the second ventilation rate and provide a second therapy signal to the therapy circuit in response to the first ventilation rate being substantially different from the second ventilation rate, and the therapy circuit is configured to deliver a first therapy regimen in response to the first therapy signal and a second therapy regimen in response to the second therapy signal.

7. The system of claim 1, further comprising a first accelerometer coupled to the processor, the first accelerometer configured to sense a first acceleration signal, and wherein the processor is configured to select one of the first ventilation rate and the second ventilation rate using the first acceleration signal in response to the difference between the first ventilation rate and the second ventilation rate being substantial.

8. The system of claim 7, wherein the processor is configured to select one of the first ventilation rate and the second ventilation rate by cross checking the first ventilation rate and the second ventilation rate with the first acceleration signal.

9. The system of claim 8, wherein the first accelerometer has a first axis of sensitivity, and further comprising a second accelerometer coupled to the processor, the second accelerometer configured to sense a second acceleration signal and having a second axis of sensitivity intersecting the first axis, and wherein the processor is configured to select one of the first ventilation rate and the second ventilation rate by cross checking the first ventilation rate and the second ventilation rate with the first acceleration signal and the second acceleration signal.

10. The system of claim 1, further including a therapy circuit coupled to the processor, the therapy circuit configured to deliver a therapy to the heart, and wherein the processor is configured to control the delivery of the therapy using the difference between the first ventilation rate and the second ventilation rate.

11. A method, comprising:
measuring a first impedance associated with a first chamber of a heart;
measuring a second impedance associated with a second chamber of the heart;
determining a first ventilation rate using the first impedance;
determining a second ventilation rate using the second impedance;
comparing the first ventilation rate to the second ventilation rate; and
adjusting a therapy using an outcome of the comparison of the first ventilation rate to the second ventilation rate.

12. The method of claim 11, wherein adjusting the therapy comprises adjusting a pacing therapy.

13. The method of claim 12, further comprising determining a difference between the first ventilation rate and the second ventilation rate, and wherein adjusting the pacing therapy comprises adjusting a pacing rate using the difference between the first ventilation rate and the second ventilation rate.

14. The method of claim 11, further including:
sensing an activity signal; and
selecting one of the first impedance and the second impedance using the activity signal in response to the outcome of the comparison indicating that the first ventilation rate is substantially different from the second ventilation rate.

15. The method of claim 14, wherein sensing the activity signal comprises sensing a first acceleration signal using a first accelerometer.

16. The method of claim 15, further comprising:
cross checking the first ventilation rate and the second ventilation rate with the first acceleration signal; and
selecting one of the first ventilation rate and the second ventilation rate using an outcome of the cross checking.

17. The method of claim 16, further comprising:
sensing a second acceleration signal using a second accelerometer;
cross checking the first ventilation rate and the second ventilation rate with the first acceleration signal and the second acceleration signal; and
selecting one of the first ventilation rate and the second ventilation rate using an outcome of the cross checking.

18. A method, comprising:
sensing a first acceleration signal indicative of activity of a heart using a first accelerometer;
sensing a second acceleration signal indicative of activity of the heart using a second accelerometer;
determining whether the first acceleration signal is substantially different from the second acceleration signal;
delivering a first therapy regimen to the heart in response to the first acceleration signal not being substantially different from the second acceleration signal;
sensing an impedance signal indicative of ventilation;
delivering a second therapy regimen to the heart in response to the first acceleration signal being substantially different from the second acceleration signal, the second therapy regimen selected as a function of the impedance signal.

19. The method of claim 18, wherein sensing the first acceleration signal and sensing the second acceleration signal comprise using a first accelerometer having a first axis of sensitivity and a second accelerometer having a second axis of sensitivity that intersects the first axis of sensitivity.

20. The method of claim 19, wherein determining whether the first acceleration signal is substantially different from the second acceleration signal comprises calculating a correlation coefficient.

* * * * *